(12) United States Patent
Becker

(10) Patent No.: US 7,854,744 B2
(45) Date of Patent: *Dec. 21, 2010

(54) METHOD FOR TREATING OBSTRUCTED PARANASAL ETHMOID SINUSES

(75) Inventor: Bruce B. Becker, Malibu, CA (US)

(73) Assignee: Acclarent, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/120,902

(22) Filed: May 15, 2008

(65) Prior Publication Data

US 2008/0208243 A1   Aug. 28, 2008

Related U.S. Application Data

(62) Division of application No. 10/259,300, filed on Sep. 30, 2002.

(51) Int. Cl.
*A61M 29/00* (2006.01)
(52) U.S. Cl. ...................................................... 606/196
(58) Field of Classification Search .................. 606/199, 606/196, 192; 604/28, 96.01, 103.01, 104, 604/500, 514; 623/1.11, 10, 66.1
See application file for complete search history.

(56) References Cited

U.S. PATENT DOCUMENTS

| | | |
|---|---|---|
| 705,346 A | 7/1902 | Hamilton |
| 3,800,788 A | 4/1974 | White |
| 3,850,176 A | 11/1974 | Gottschalk |
| 3,859,993 A | 1/1975 | Bitner |
| 4,102,342 A | 7/1978 | Akiyama et al. |
| 4,299,227 A | 11/1981 | Lincoff |
| 4,338,941 A | 7/1982 | Payton |
| 4,437,856 A | 3/1984 | Valli |
| 4,459,977 A | 7/1984 | Pizon et al. |
| 4,606,346 A | 8/1986 | Berg et al. |
| 4,771,776 A | 9/1988 | Powell et al. |
| 4,796,629 A | 1/1989 | Grayzel |
| 4,811,743 A | 3/1989 | Stevens |
| 4,883,465 A | 11/1989 | Brennan |
| 4,946,466 A | 8/1990 | Pinchuk et al. |
| 5,021,043 A | 6/1991 | Becker et al. |
| 5,024,650 A | 6/1991 | Hagiwara et al. |
| 5,169,386 A | 12/1992 | Becker et al. |
| 5,207,695 A | 5/1993 | Trout, III |
| 5,221,260 A | 6/1993 | Burns et al. |
| 5,252,183 A | 10/1993 | Shaban et al. |
| 5,270,086 A | 12/1993 | Hamlin |
| 5,336,163 A | 8/1994 | DeMane et al. |
| 5,346,075 A | 9/1994 | Nichols |

(Continued)

OTHER PUBLICATIONS

Gottmann et al, "Balloon dilation of recurrent ostial occlusion of the frontal sinus". Abstract No. B-04353 and slides, ECR, Mar. 2 2001.*

(Continued)

*Primary Examiner*—Todd E Manahan
*Assistant Examiner*—Jonathan A Hollm
(74) *Attorney, Agent, or Firm*—Steptoe & Johnson LLP

(57) ABSTRACT

A method of treating a patient's ethmoid sinus. A balloon of a balloon catheter is inflated in a space associated with the ethmoid sinus to enlarge the space. The space remains enlarged after the balloon catheter is removed.

16 Claims, 9 Drawing Sheets

U.S. PATENT DOCUMENTS

| | | | |
|---|---|---|---|
| 5,391,179 | A | 2/1995 | Mezzoli |
| 5,411,477 | A | 5/1995 | Saab |
| 5,454,817 | A | 10/1995 | Katz |
| 5,546,964 | A | 8/1996 | Stangerup |
| 5,578,048 | A | 11/1996 | Pasqualucci et al. |
| 5,584,827 | A | 12/1996 | Korteweg et al. |
| 5,601,594 | A | 2/1997 | Best |
| 5,792,100 | A | 8/1998 | Shantha |
| 5,824,044 | A | 10/1998 | Quiachon et al. |
| 5,827,224 | A | 10/1998 | Shippert |
| 5,904,701 | A | 5/1999 | Daneshvar |
| 5,928,192 | A | 7/1999 | Maahs |
| 5,931,811 | A | 8/1999 | Haissaguerre et al. |
| 5,997,562 | A | 12/1999 | Zadno-Azizi et al. |
| 6,027,478 | A | 2/2000 | Katz |
| 6,123,697 | A | 9/2000 | Shippert |
| 6,663,589 | B1 * | 12/2003 | Halevy .................. 604/96.01 |
| 6,716,813 | B2 | 4/2004 | Lim et al. |
| 6,776,772 | B1 | 8/2004 | Vrijer et al. |
| D501,677 | S | 2/2005 | Becker |
| 7,184,827 | B1 | 2/2007 | Edwards |
| 2004/0043052 | A1 * | 3/2004 | Hunter et al. ............... 424/426 |
| 2004/0064083 | A1 | 4/2004 | Becker |
| 2004/0064150 | A1 | 4/2004 | Becker |
| 2007/0073269 | A1 | 3/2007 | Becker |
| 2008/0208243 | A1 | 8/2008 | Becker |

OTHER PUBLICATIONS

Shah, "Functional Endoscopic Sinus Surgery". Bombay Hospital Journal, Oct. 1999; fount at www.bhj.org/journal/1999_4104_oct99/sp_659.htm.*

Robinson, "Pressure Treatment of Maxillary Sinusitis", JAMA, May 31, 1952, pp. 436-440.*

Shah, "Functional Endoscopic Sinus Surgery", Bombay Hospital Journal, Oct. 1999; found at www.bhj.org/journal/1999_4104_oct99/sp_659.htm.*

Ijaduola, T.G.A, "Use of a Foley Catheter for Short-Term Drainage in Frontal Sinus Surgery", The Journal of Laryngology and Otology Apr. 1989, vol. 103, pp. 375-378.

Gottman, et al., "Balloon Dilatation of Recurrent Ostial Occlusion of the Frontal Sinus, Abstract", OASIS Online Abstract Submission and Invitation System.

Robison, J. Mathews, "Pressure Treatment of Maxillary Sinusitis", J.A.M.A. May 31, 1952.

Robison, J. Mathews, "Pressure Treatment of Maxillary Sinusitis", Texas State Journal of Medicine, May 1951, pp. 281-288.

Strohm, et al., "Treatment of Stenoses of the Upper Airways by Balloon Dilation", 83rd Annual Conference of the Union of Southwest German Ear, Nose and Throat Specialists, Sep. 25, 1999.

File History of U.S. Patent No. 7,462,175.

Gottman, et al., "Balloon Dilatation of Recurrent Ostial Occlusion of the Frontal Sinus, Abstract", ECR presentation.

Kennedy, David W., M.D., et al., "Diseases of the Sinuses Diagnosis and Management", Copyright 2001 by B.C. Decker Inc.

Schaefer, Steven D., M.D., "Rhinology and Sinus Disease a Problem-Oriented Approach", Copyright 1988 by Mosby, Inc.

Friedman, Michael, M.D., et al., "Operative Techniques in Otolaryngology-Head and Neck Surgery", vol. 12, No. 2, Jun. 2001, pp. 60-65.

Lanza, Donald C., "Postoperative Care and Avoiding Frontal Recess Stenosis", International Advanced Symposium, Jul. 21-24, 1993.

Office Action dated Mar. 23, 2009 in U.S. Appl. No. 11/804,309.

Office Action dated Mar. 23, 2009 in U.S. Appl. No. 11/926,326.

Yanagisawa et al., Anterior and Posterior Nasal Fontanelles, Ear, Nose, & Throat Journal, Jan. 2001: 80, 1, pp. 10-12.

USPTO Office Action dated Oct. 29, 2008 in U.S. Appl. No. 11/347,147, filed Feb. 2, 2006.

USPTO Office Action dated Feb. 4, 2009 in U.S. Appl. No. 11/347,147, filed Feb. 2, 2006.

USPTO Office Action dated Aug. 6, 2009 in U.S. Appl. No. 11/347,147, filed Feb. 2, 2006.

USPTO Office Action dated Nov. 17, 2008 in U.S. Appl. No. 12/118,931, filed May 12, 2008.

USPTO Office Action dated Mar. 4, 2009 in U.S. Appl. No. 12/118,931, filed May 12, 2008.

USPTO Office Action dated Jul. 30, 2009 in U.S. Appl. No. 12/118,931, filed May 12, 2008.

USPTO Office Action dated Nov. 17, 2008 in U.S. Appl. No. 12/117,582, filed May 8, 2008.

USPTO Office Action dated Mar. 3, 2009 in U.S. Appl. No. 12/117,582, filed May 8, 2008.

USPTO Office Action dated Aug. 6, 2009 in U.S. Appl. No. 12/117,582, filed May 8, 2008.

USPTO Office Action dated Aug. 6, 2009 in U.S. Appl. No. 12/117,961, filed May 9, 2008.

Friedman, Michael, MD et al., "Middle turbinate medialization and preservation in endoscopic sinus surgery," Otolaryngology-Head and Neck Surgery, vol. 123, No. 1, Part 1, pp. 76-80.

* cited by examiner

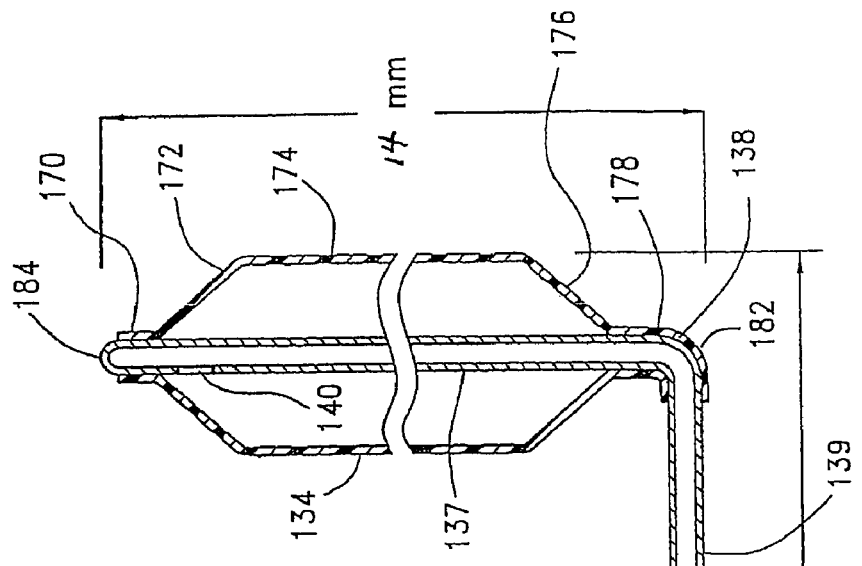
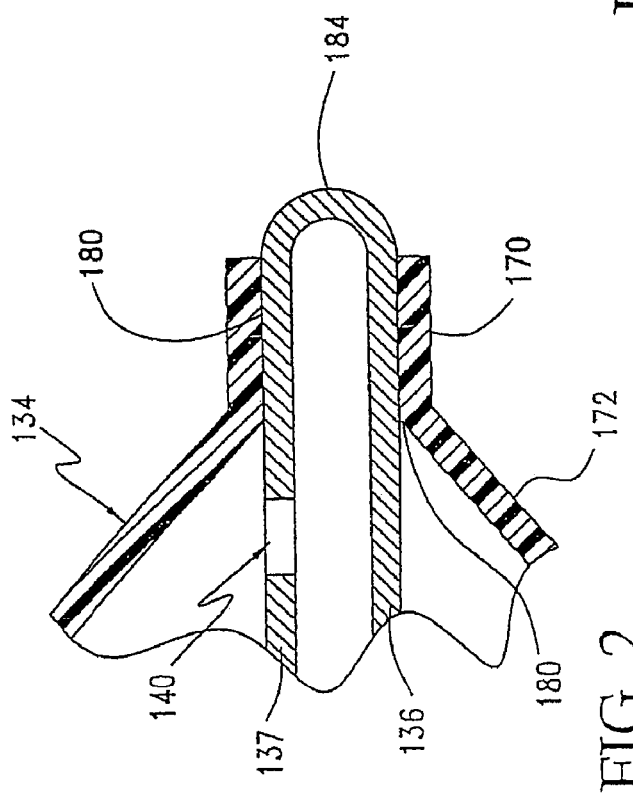
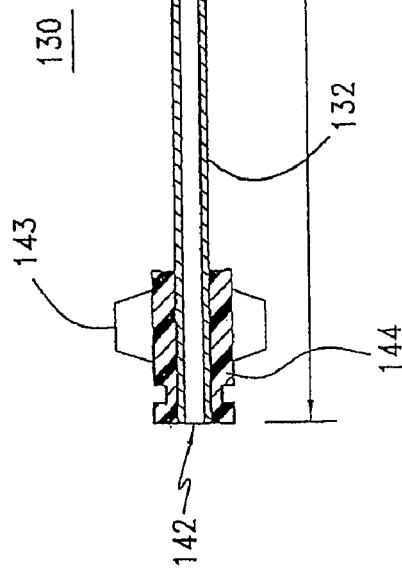
FIG. 1
FIG. 2

METHOD FOR TREATING OBSTRUCTED PARANASAL ETHMOID SINUSES

PRIOR APPLICATION

This is a divisional of U.S. patent application Ser. No. 10/259,300, filed Sep. 30, 2002.

FIELD OF THE INVENTION

This invention relates to balloon catheters and methods using such catheters for treating paranasal sinuses.

BACKGROUND

To fully understand the invention, it is necessary to consider the anatomy and physiology of the sinus system. FIGS. 4-16, which show various steps of methods of the invention, also show important features of sinus anatomy. The maxillary sinus 21 lies lateral to the nasal cavity 38, inferior to the eye orbit 23 and superior to the palate or roof of the mouth. The medial wall of the maxillary sinus forms the lateral nasal wall 44 inferiorly. The frontal sinus 35 (FIG. 16) lies above the orbit and its floor is formed by the frontal bone and is contiguous with part of the orbital roof. The right and left frontal sinuses are divided by the interfrontal septum. The frontal sinus drains into the nasal cavity and its outflow tract is in the inferomedial sinus, which connects to the frontonasal duct 36. Frontonasal duct 36 empties into the nasal cavity through lateral nasal wall 44 under the middle turbinate 20.

The ethmoid sinus is divided into anterior and posterior ethmoid air cells 29 and 31. The ethmoid sinus consists of multiple spaces or cells divided by thin bony septae. The ethmoid sinus is contained in the ethmoid bone. The lateral wall of the ethmoid sinus composes the medial wall of the orbit. The medial wall of the ethmoid sinus composes the lateral wall 44 of the nasal cavity superiorly. Anterior ethmoid air cells 29 drain through lateral nasal wall 44 into the middle meatus 22 beneath middle turbinate 20.

The sphenoid sinus 39 is posterior to the ethmoid sinus 29 and 31. Sphenoid sinus 39 has a lateral wall that is adjacent to the optic nerve, carotid artery, and cavernous sinus. The floor of sphenoid sinus 39 lies above maxillary sinus 21 and pterygopalatine fossa. Lateral nasal wall 44 is partially covered by inferior 46, middle 20, and superior 17 turbinates.

Sinus physiology will now be considered. The mucosa of nasal cavity 38 contains secretory elements (mucosal glands and goblet cells) and a dense ciliary layer. The paranasal sinuses are covered by a similar mucosa, although the secretory cells and cilia may be sparser in the more remote areas of the sinuses. The secretory cells produce a large volume of mucus that is normally actively transported by the cilia (mucociliary transport) in a specific pattern (not a gravity dependant pattern) from the sinus through the opening between the sinus and the nasal cavity (sinus ostium). Cellular debris and bacteria are transported in the mucus from the sinus cavity through the ostium into the nose.

Inflammation of the sinus and nasal mucosa causes hyperemia, lymphatic swelling, stasis in the blood and lymphatic pathways and leads to increased secretion of mucus and reduced mucociliary transport. The inflammation may be caused by allergies, noxious agents, nasal polyps, and other factors. Over time there is a pathologic increase in inflammatory cells, ground substance, and fibers with a permanent disruption of mucociliary transport and lymphatic drainage. An obstruction of the narrow ducts and ostia between the paranasal sinuses and nasal cavity develops, resulting in a vicious cycle of increased secretions, edema, and ultimately organized connective tissue and mucosal hyperplasia. Bacteria are not cleared from the sinuses and multiply in the fertile inflammatory environment worsening the chronic sinus inflammation (sinusitis).

Treatment with antibiotics, corticosteroids in nasal sprays or systemically, and antihistamines may result in resolution of sinusitis. However some patients become resistant to medical treatment and surgery becomes necessary.

Modem sinus surgery is usually performed endoscopically and is based on the principle of restoring patency of the sinus ducts and ostia by enlarging the opening and allowing mucociliay clearance of mucus from the sinus into the nose to resume. If mucociliary clearance is re-established, then the inflammatory changes in the sinus mucosa described above will resolve. In classic sinus surgery, an incision was made along the side of the nose in the medial canthus to access the ethmoid or sphenoid sinuses. This incision could be extended to beneath the medial half of the brow to also access the frontal sinus. An incision through the gums above the upper teeth and creation of a large bony opening in the maxilla with excision of large areas of sinus mucosa was used to perform maxillary sinus surgery. A large opening was created through the medial wall of the maxillary sinus into the nose in the inferior meatus (maxillary antrostomy) to allow postoperative drainage of the sinus.

The development of endoscopic sinus surgery allowed sinus surgery to be performed from an intranasal approach, thus eliminating the need for external incisions, the creation of very large bony openings, and reducing morbidity. However, endoscopic sinus surgery requires the excision of large areas of bone and nasal mucosa and has reported complications of blindness from damage to the optic nerve, double vision from damage to the orbit and medial rectus muscle, damage to the nasolacrimal duct resulting in tearing and dacryocstitis, leakage of central nervous system fluid and infection of the brain and meninges, loss of the sense of taste, and pain and neuralgia of the face and scalp, and infection of the skull base.

As shown in U.S. Pat. Nos. 5,021,043 and 5,169,386, I have previously co-invented balloon catheters for use in the lacrimal system. In my application "Transnasal Method and Catheter for Lacrimal System," filed herewith, I teach that a balloon catheter can be introduced transnasally to treat the lacrimal system.

A review of the prior art shows a number of patents (Katz U.S. Pat. No. 6,027,478; Brennan U.S. Pat. No. 4,883,465; Akiyama U.S. Pat. No. 4,102,342; Payton U.S. Pat. No. 4,338,941; Katz U.S. Pat. No. 5,454,817; Stangerup U.S. Pat. No. 5,546,964 and Shippert U.S. Pat. No. 5,827,224) which teach the use of expandable devices (usually a balloon) into the nasal cavity or sinuses. Most of these are for the treatment of nose bleeds or the control of bleeding.

A number of articles disclose the use of a balloon catheter in sinuses to hold fractured bones in place, stop bleeding by tamponade, prevent fluid from flowing out of the nose into the pharynx, or to maintain a low intranasal air pressure. In one case, a catheter was used to stent a duct after surgery; and the balloon was inflated in the sinus to deep the stent in position. However, there are no teachings in the prior are to use a balloon catheter to create a new opening from a sinus into the nose, to dilate an ostium or duct, or excise a sinus. A balloon was never used to directly treat sinus disease.

SUMMARY

The present inventions teaches the use of sinus balloon catheters to treat sinus disease by creating a new opening from a sinus into the nose, to dilate a sinus ostium or duct, or to excise a sinus. The balloon catheters of the invention constitute a set of catheters having different configurations and dimensions suitable for the treatment of different parts of the paranasal sinus system. The catheters comprise a hypotube formed of stainless steel of sufficient stiffness and column strength to act as a pushable member to be pushed through a surgically prepared small, tight opening from a sinus into the nose, through a sinus ostium or duct, or into a sinus cavity. The small opening may be created surgically or may be the natural ostium or duct of the sinus. In other words, the balloon acts as an expandable and contractable member which in a smaller, contracted or deflated profile can be pushed into a space in the patient's sinus and then expanded to a larger, expanded or inflated profile. After waiting a period, the expandable and contractable member can be contracted or deflated and removed to dilate the space.

One of the balloon catheters used in the invention has a proximal segment and a circular bend placing a distal segment at an angle of 70 degrees to 115 degrees, preferably 90 degrees to the proximal segment. A balloon is mounted over the distal segment which has a slot permitting a fluid under the pressure applied to the proximal end of the proximal segment to inflate the balloon. In other words, the tube acts as a fluid supply conduit in fluid communication with the balloon.

The angled distal segment allows the surgeon to rotate or shift the position of the long proximal catheter shaft, thus positioning the distal segment to enter from the nasal cavity into the sinus at various angles appropriate to each individual patient. The balloon catheter with the 90 degree angle is used to treat maxillary and frontal sinus disease.

The distal segment of the balloon catheter from the outside of the bend to the end of the catheter is 14 mm. The length of the distal segment is short enough to allow it to be rotated within the nasal cavity and thus enter from the nasal cavity into the sinus at the desired angle. The distal segment is long enough to allow a balloon of sufficient length and diameter to be attached to the hypotube for dilation of an opening through the lateral nasal and sinus wall, duct, or ostium. The balloon material is attached with adhesive to the very distal portion of the distal segment and to the proximal portion of the distal segment, the bend, and the very distal portion of the long proximal segment. A longer working segment of balloon can be used because the area of adhesion of the balloon includes the bend and the distal portion of the proximal segment. A 9 mm inflated diameter angled balloon is used to treat the maxillary sinus and a 5 mm inflated diameter angled balloon is to treat the frontal sinus.

Another balloon catheter of the invention is straight or has a minimal angle at the junction of the distal segment and the proximal segment. This balloon catheter is used for ethmoidectomy and sphenoid sinusotomy and uses a balloon with an inflated diameter of 9 mm. Each of the balloon catheters of the invention have a sufficiently small deflated profile to fit through the sinus ostium, duct, or opening in the nasal wall or scar tissue into the sinus.

It is useful to apply a lubricious coating to the balloon material to facilitate pushing it through the lateral nasal wall and sinus wall into the sinus. The proximal catheter shaft has a luer lock with wings or an expansion to allow the catheter to be attached to tubing from the inflation device. The wings allow the surgeon to more easily manipulate the balloon catheter.

The methods of the invention open or enlarge an obstructed or narrowed ostium or duct of a sinus using a balloon and allow the sinus to drain into the nose. This is accomplished without causing damage to the surrounding structures such as the optic nerve, extraocular muscles that move the eye, the orbit, brain, meninges, or nasolacrimal duct.

Another method of the invention removes a sinus and cures sinus disease without damage to the surrounding structures such as the optic nerve, extraocular muscles, orbit, brain, meninges, and nasolacrimal duct. The methods of the invention are useful for opening a sinus ostium or duct which has been narrowed or obstructed by scar tissue from previous surgery or trauma, for creating a new opening in the wall of a sinus which has scar tissue to allow proper drainage of the sinus into the nose, and for removing a sinus which has scar tissue.

The methods of the invention include a balloon catheter antrostomy of the maxillary ostium, a balloon catheter middle meatal maxillary antrostomy, a balloon catheter inferior meatal antrostomy, a balloon catheter ethmoidectomy of the anterior ethmoid sinus, a balloon catheter ethmoidectomy of the posterior ethmoid sinus, a balloon catheter sinusotomy of the sphenoid sinus, and a balloon catheter frontal sinusotomy.

BRIEF DESCRIPTION OF THE DRAWING

FIG. 1 is a schematic drawing of one embodiment of the sinus balloon catheter of the invention;

FIG. 2 is a closeup schematic drawing of the tip of the distal segment of the sinus balloon catheter of FIG. 1;

FIG. 3a is a closeup schematic drawing of the tip of the sinus balloon catheter of FIG. 3;

DESCRIPTION OF THE PREFERRED EMBODIMENT(S)

Figure 3:
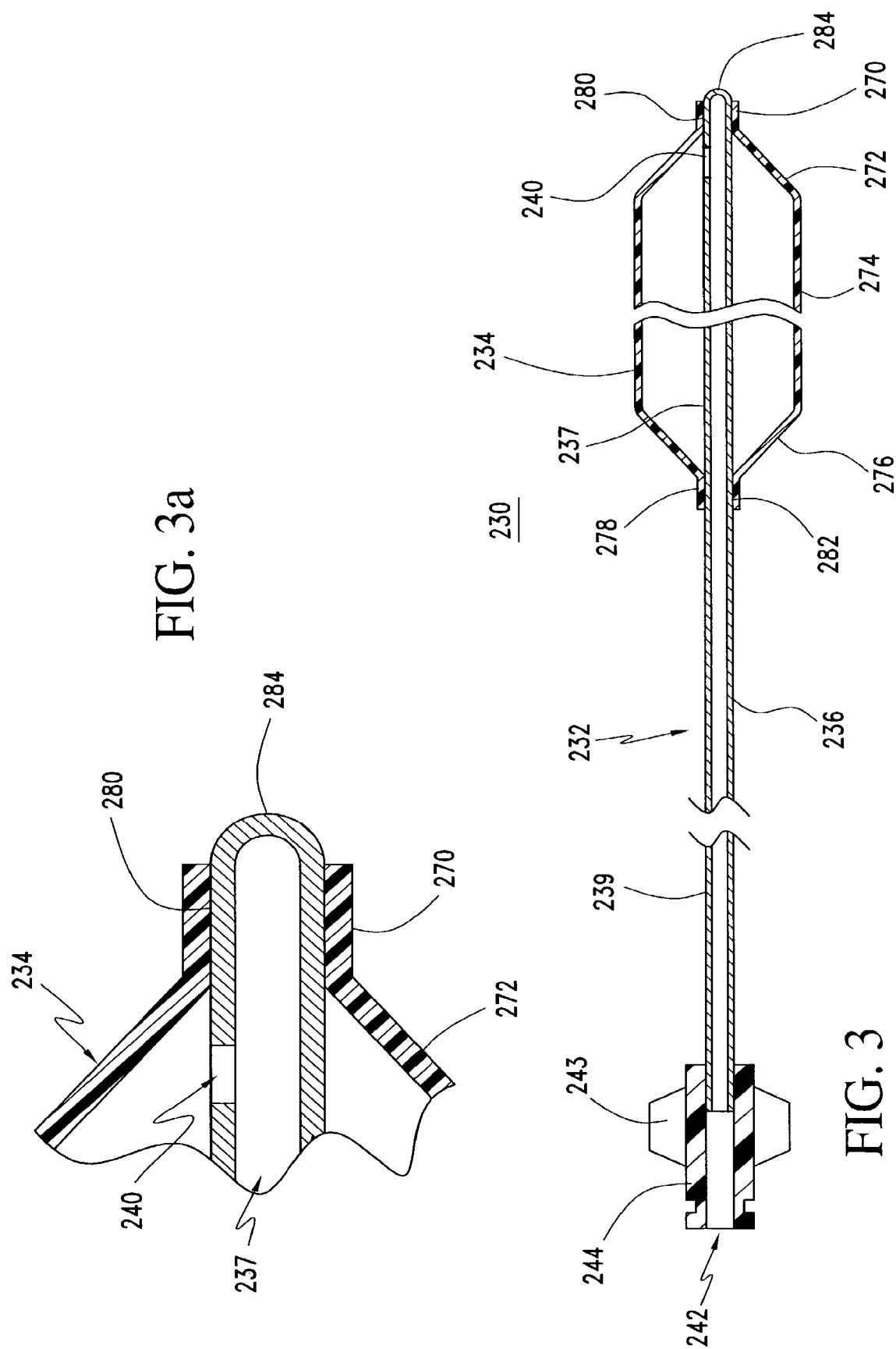
FIG. 3 is a schematic drawing of a second embodiment of a sinus balloon catheter of the invention.

As shown in FIGS. 1 and 2, a first embodiment of a sinus balloon catheter 130 of the invention is assembled from a tube 136, preferably a stainless steel hard tempered hypotube which has a circular bend 138 of 0.13 inch radius such that distal segment 137 is oriented 70 degrees to 115 degrees, preferably 90 degrees, to proximal segment 139. A slot 140 is provided in segment 137. The distance from the distal tip 184 of distal segment 137 to the outer wall of proximal segment 139 of hypotube 136 is 4 mm to 30 mm, preferably 14 mm, as shown in FIG. 1. The distal tip 184 of the hypotube 136 is closed, whereas the proximal end 142 is open. However, the lumen of tube 136 may be closed in distal segment 137, up to 10 mm from distal tip 184, allowing distal tip 184 to remain open. In either case, tube 136 is closed distally of slot 140. The proximal end 142 of hypotube 136 is inserted into a mold for forming luer 144 and plastic is injected into the mold to form luer 144 attached to the end of proximal segment 139. The inner diameter of the luer 144 matches the external diameter of the hypotube 136. The luer 144 has wings 143 or other enlargement or expansion on it to enable the surgeon to better hold and manipulate balloon catheter 130. Catheter 130 is 4 inches to 10 inches long, preferable 6 inches in length as measured from proximal end 142 to distal tip 184, as shown in FIG. 1. The wall 132 of tube 136 should be of such thickness that the tube has sufficient stiffness and column strength with marked resistance to lateral bending that distal segment 137 can be pushed through a prepared small, tight opening from a sinus into the nose, pushed through a sinus ostium or duct, or pushed into a sinus cavity which may require considerable pressure in some cases. It has been found that a tube with a wall thickness of at least 0.035 inch will be satisfactory. A preferred tube has an outer diameter of 0.083 inch and an inner diameter of 0.039 inch with a wall thickness of 0.044 inch.

Port 140 in distal segment 137 is formed by inserting temporarily a discardable wire segment into the tube 136. This is done before inserting hypotube 136 into luer 144. A transverse slot is cut in the tube 136 approximately 2 mm to 14 mm, preferably 4 mm, from its distal end 184 to form port 140. The slot extends in depth to approximately one third of the diameter of tube 136. A wire wheel is used to remove any burrs, and the discardable core wire is removed and discarded.

A balloon 134 is preferably formed of polyethylene terephthalate and has a length of approximately 4 mm to 30 mm, preferably 14 mm, and a working inflated diameter of 2 mm to 14 mm, preferably 9 mm, for use in the sinus system, except for use in the nasofrontal duct where the preferable inflated working diameter is 5 mm. The balloon has a distal neck 170, a distal tapered region 172, a center region 174, a proximal tapered region 176, and a proximal neck 178. During installation, tube 136 is cleaned with isoproponol and then coated with a primer, "Loctite 770." The balloon is placed over the distal end of tube 136 to align the distal end of distal neck 170 with distal end 184 of tube 136. An adhesive, such as cyanoacrylate, is used. An acceptable adhesive "Loctite 4081" is available from Loctite Corporation. The adhesive is applied to distal end of distal neck 170 and the proximal end of proximal neck 178 to form bonds 180 and 182, respectively. The adhesive is applied to the balloon necks 170, 178 using a small mandrel such as a wire approximately 0.010 inch to 0.014 inch in diameter. The adhesive wicks into the necks due to capillary action. Proximal neck 178 may be bonded on distal segment 137 of tube 136 or extend over bend 138 onto the distal end portion of proximal segment 139 of tube 136. Extension of the proximal neck 178 onto bend 138 and proximal segment 139 allows a greater length of the working diameter, i.e., center region 174, to be on distal segment 137 of tube 136.

A second embodiment of sinus catheter of the invention is shown in FIG. 3. The catheter 230 is assembled from a tubular body 232, formed of stainless steel hard tempered hypotube 236 which is straight or has a mild circular bend distally such that distal segment 237 is oriented 130 to 180, preferably 180 degrees, to a long proximal segment 239. The distance from the distal tip 284 of distal segment 237 to the outer wall of proximal segment 239 of hypotube 236 is 10 to 100 mm, preferably 16 mm. The distal tip 284 of the hypotube 236 preferably is closed whereas the proximal end 242 is open. However, the lumen of tube 236 may be closed 0 to 10 mm from distal tip 284 allowing distal tip 284 to be open. The proximal end 242 of hypotube 236 is inserted into a mold for forming luer 244. Heated plastic is injected into the mold to form luer 244 attached to the end of proximal segment 239. The inner diameter of luer 244 matches the external diameter of hypotube 236. The luer 244 has wings 243 or expansions on it to enable the surgeon to better hold and manipulate balloon catheter 230.

Catheter 230 has a port 240 in distal segment 237 which is formed by inserting temporarily a discardable wire segment into the tube 236. This is done before inserting hypotube 236 into luer 244. A transverse slot is cut in tube 236 approximately 2 to 14 mm, preferably 4 mm, from its distal end 284 to form port 240. The slot extends in depth to approximately ⅓ of the diameter of tube 236. A wire wheel is used to remove any burrs, and the discardable core wire is removed and discarded.

It is desirable for the catheter 230 to have column strength and marked resistance to lateral bending. The deflated catheter must be capable of being pushed through an initial prepared small opening in the nasal or sinus wall, an ostium or duct, and into a sinus cavity. This may require considerable pressure in some cases.

A balloon 234, preferably formed of polyethylene terephthalate, has a length of approximately 4 to 30 mm, preferably 14 mm, and an inflated working diameter of 3 to 15 mm, preferably 9 mm. The balloon has a distal neck 270, a distal tapered region 272, a center region 274, a proximal tapered region 276, and a proximal neck 278. Necks 270 and 278 are bonded to hypotube 236, forming bonds 280 and 282, in the same manner as is described above with respect to the attachment of necks 178 and 170 to hypotube 136.

As will be described below, angled catheter 130 and "straight" catheter 230 will be used in different method steps for treating various prepared openings, naturally occurring ostia and ducts, and sinus cavities. It is also to be noted that dimensions of the catheters are selected to accommodate different conditions in the paranasal sinus system. For example, the outer diameters of the distal segments with the balloon deflated are selected so that the respective distal segments with the balloon deflated will fit snugly with the prepared openings, natural ostia or ducts and sinus cavities into which these distal segments are to be pushed. As already mentioned, the working inflated diameters of the balloons differ depending on the size required to treat different parts of the paranasal sinus system. Accordingly, the surgeon must, at the time surgery is begun, have available a set of sinus balloon catheters which are angled or straight, the balloons of which have appropriate inflated working diameters, and which have appropriate outer diameters with the balloon deflated that will enable the catheter in question to be pushed into the respective prepared opening, natural ostium or duct or sinus cavity to be excised.

Figure 4:
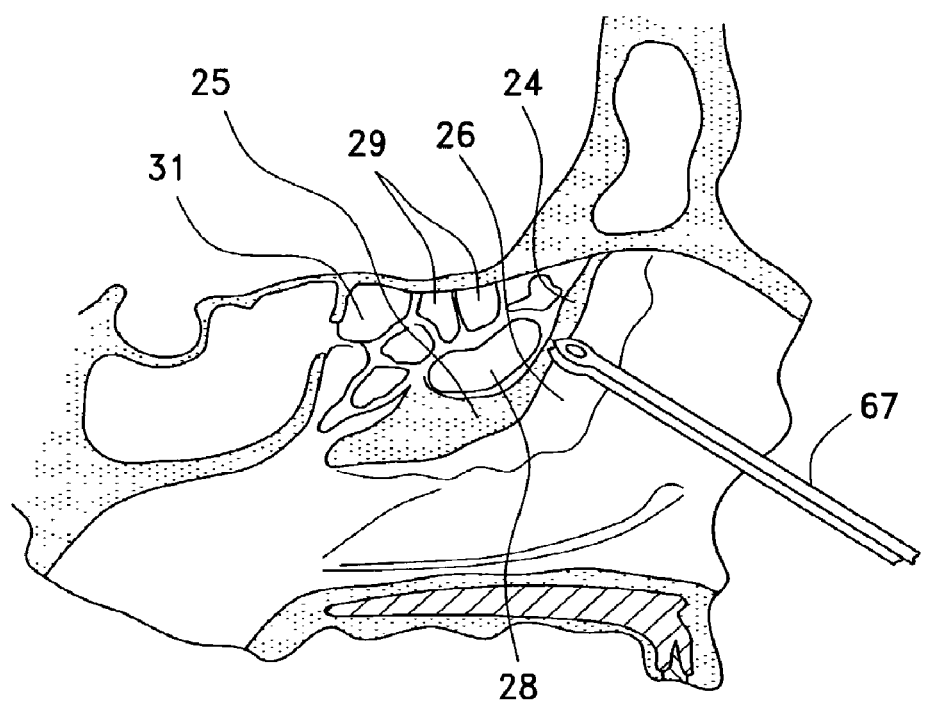
FIG. 4 is a schematic drawing of a step of a method of the invention, showing the uncinate process being removed with a punch to expose the ethmoid infundibulum and semilunar hiatus.
Figure 5:
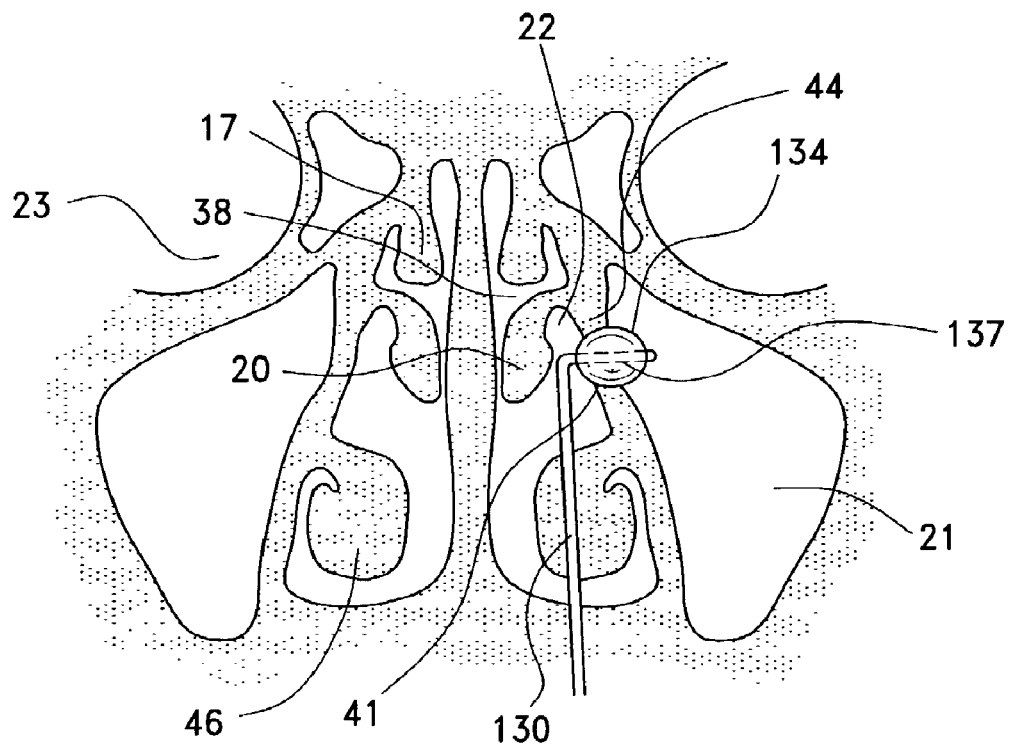
FIG. 5 is a schematic drawing of another step of the method of FIG. 4 showing the sinus balloon catheter dilating and thereby enlarging the ostium of the maxillary sinus.

Turning to FIGS. 4 and 5, in a method of performing balloon catheter antrostomy of the maxillary ostium, the middle turbinate 20 is retracted medially to gain access to the middle meatus 22. In some cases the middle turbinate is resected. The ethmoid infundibulum 24 is exposed by using cutting forceps 67 to remove part of the uncinate process 26 (FIG. 4). Distal segment 137 of balloon catheter 130 is then pushed through the maxillary ostium 41 (which is in ethmoid infundibulum 24) into the maxillary sinus 21. As seen in FIG. 5, balloon 134 is inflated to 9 bars (atmospheres) for 20 seconds then deflated. Distal segment 137 of balloon catheter 130 is slightly repositioned to insure full dilation and inflated again to 9 bars for 20 seconds. Balloon 134 is then deflated, and catheter 130 is removed from the now enlarged ostium 41.

Figure 6:
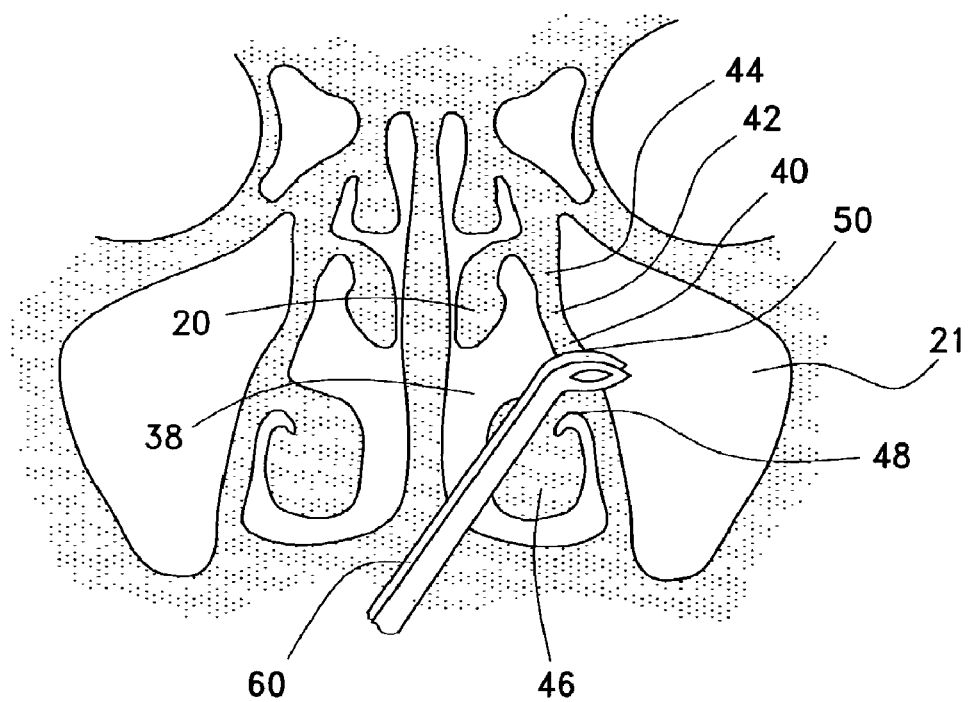
FIG. 6 is a schematic drawing of a step of a second method of the invention showing the Blakesely punch creating a small opening in the fontanelle of the lateral nasal wall in the middle meatus thus creating a communication between the maxillary sinus and nasal cavity.
Figure 7:
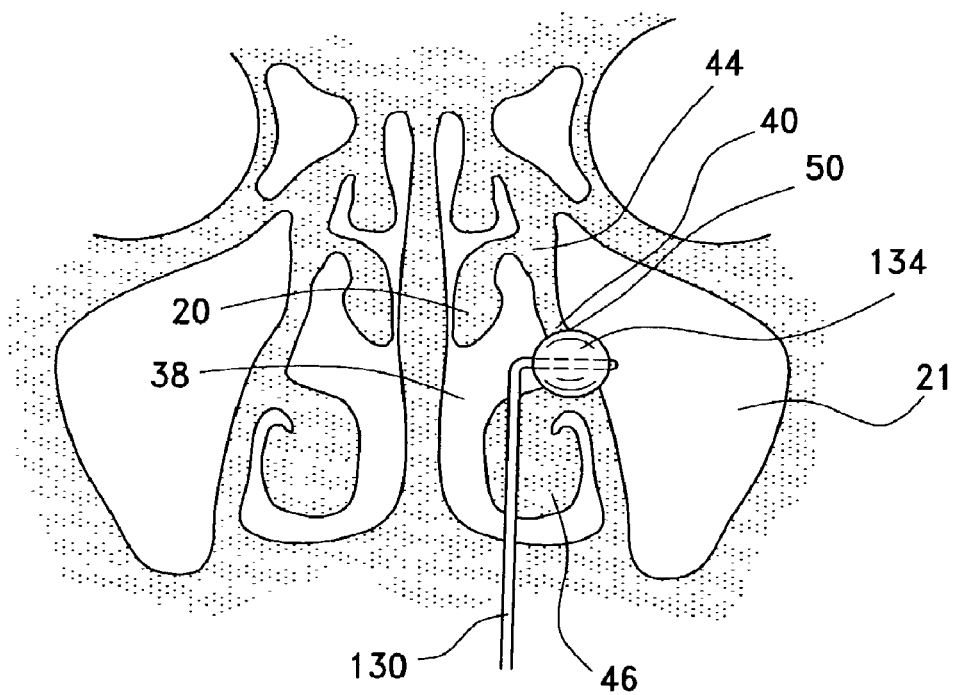
FIG. 7 is a schematic drawing of another step of the method of FIG. 6 showing the sinus balloon catheter dilating the opening in the fontanelle of the lateral nasal wall in the middle meatus thus creating a large communication opening (antrostomy) for drainage from the maxillary sinus into the nasal cavity.

Turning to FIGS. 6 and 7, in a method of performing a middle meatal maxillary antrostomy, an initial opening is made in the fontanelle 40 (section of thin membranous tissue without bone of the medial maxillary sinus wall 42 which is also a portion of the lateral nasal wall 44). This is performed by bringing a 45 degree upbiting Blakesely punch 60 into nasal cavity 38 along the lateral nasal wall 44 just superior to the inferior turbinate 46 at the midpoint of its horizontal axis to perforate fontanelle 40 to create a new 3 mm opening 50 (FIG. 6). The punch 60 is removed, and sinus balloon catheter 130 is brought into nasal cavity 38 and pushed into the new opening 50 in fontanelle 40 of lateral nasal wall 44 (FIG. 7). Balloon 134 is inflated to 9 bars for 20 seconds then deflated. Balloon catheter 130 is slightly repositioned in the enlarged opening 50 to insure thorough dilation and inflated again to 9 bars for 20 seconds. Balloon catheter 130 is then deflated and withdrawn from opening 50 and nasal cavity 38.

Figure 8:
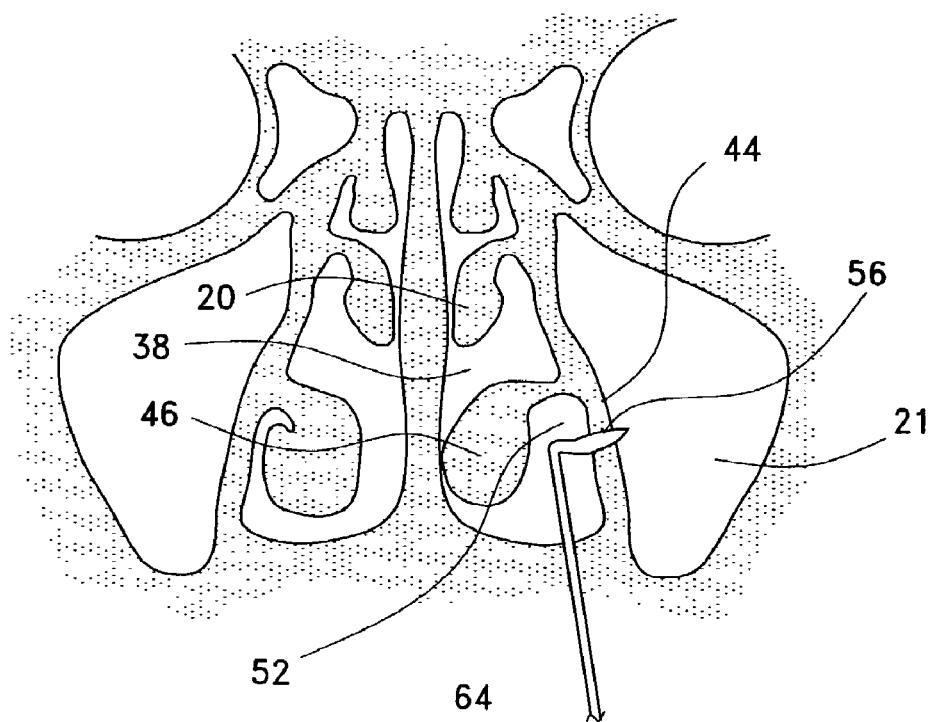
FIG. 8 is a schematic drawing of a step of a third method of the invention showing the dissector perforating the lateral nasal wall in the inferior meatus into the maxillary sinus.
Figure 9:
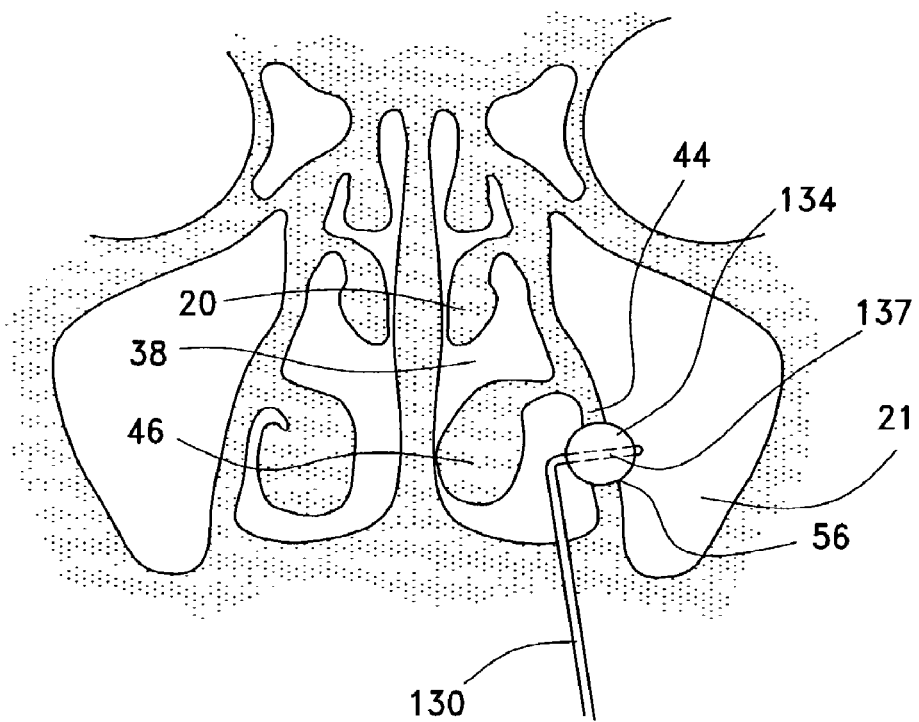
FIG. 9 is a schematic drawing of another step of the method of FIG. 8 showing the sinus balloon catheter dilating the opening in the lateral nasal wall in the inferior meatus thus creating a large antrostomy for drainage from the maxillary sinus into the nasal cavity.

As seen in FIGS. 8 and 9, in a method of inferior meatal antrostomy, the inferior turbinate 46 has been displaced medially. A sharp dissector 64 is introduced into nasal cavity 38 and used to perforate lateral nasal wall 44 in the inferior meatus 52 to create an opening 56 in lateral nasal wall 44 (FIG. 8). Dissector 64 is withdrawn from nasal cavity 38. The deflated balloon catheter 130 is introduced into the nasal cavity 38, and distal segment 137 of balloon catheter 130 is pushed through opening 56 in lateral nasal wall 44. The balloon 134 is inflated to 9 bars for 20 seconds then deflated. Deflated balloon 134 is slightly repositioned to assure total dilation of the opening 56. A second dilation of the balloon 134 to a pressure of 9 bars for 20 seconds is performed. The balloon catheter 130 is then deflated and withdrawn from opening 56 and nasal cavity 38.

Figure 10:
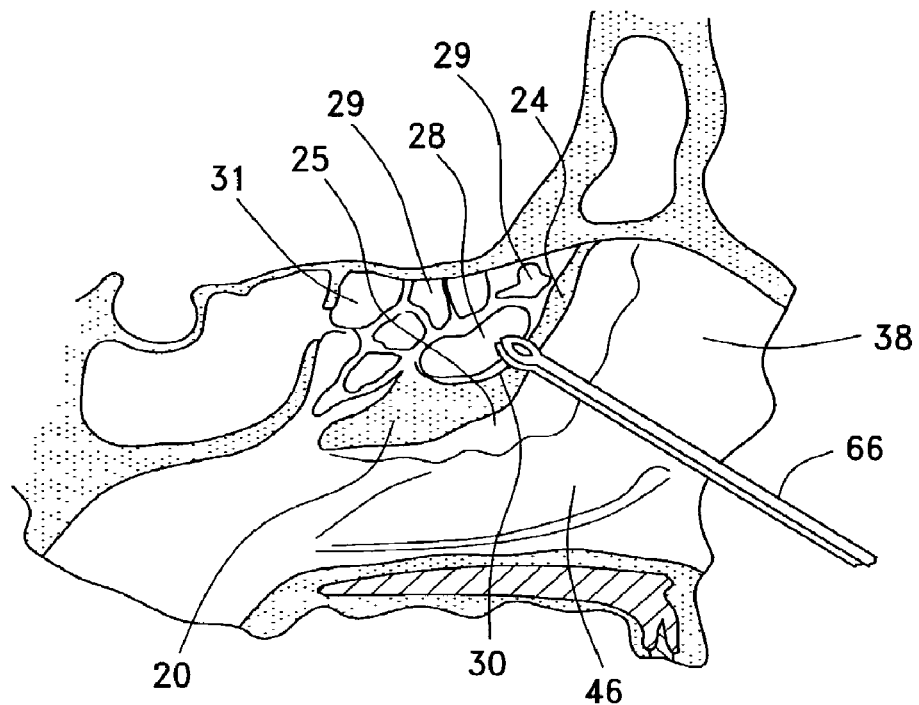
FIG. 10 is a schematic view of a fourth method of the invention showing the cutting forceps making a new opening in the anterior wall of the ethmoid bulla.
Figure 11:
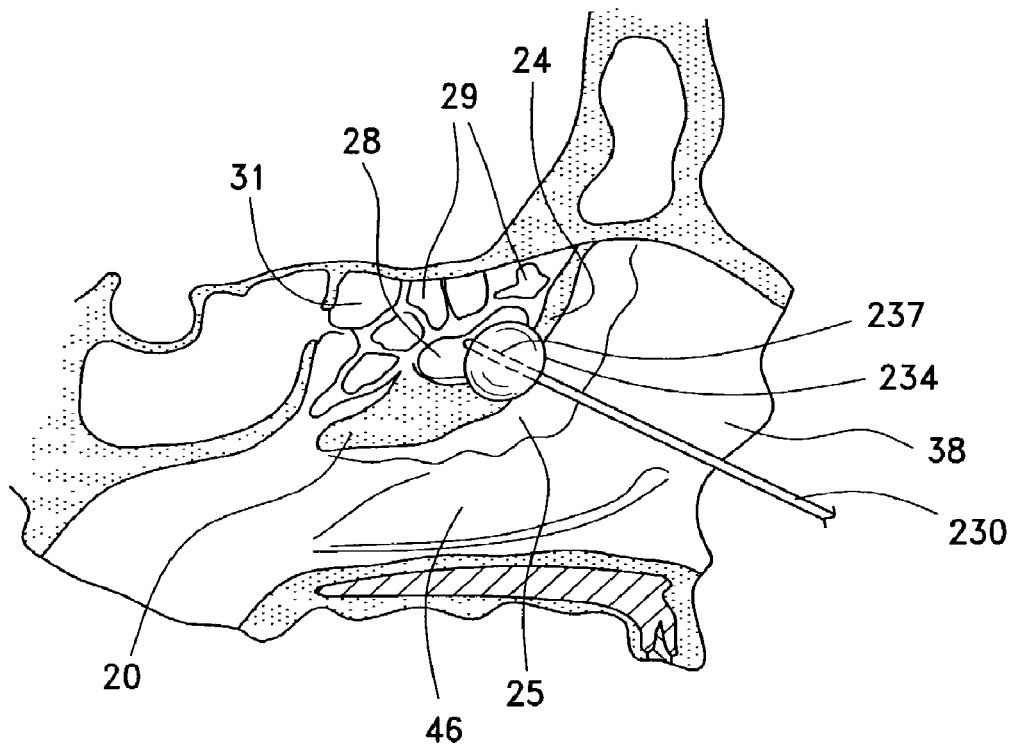
FIG. 11 is a schematic view of another step of the method of FIG. 10 showing the straight sinus balloon catheter dilating the ethmoid bulla.
Figure 12:
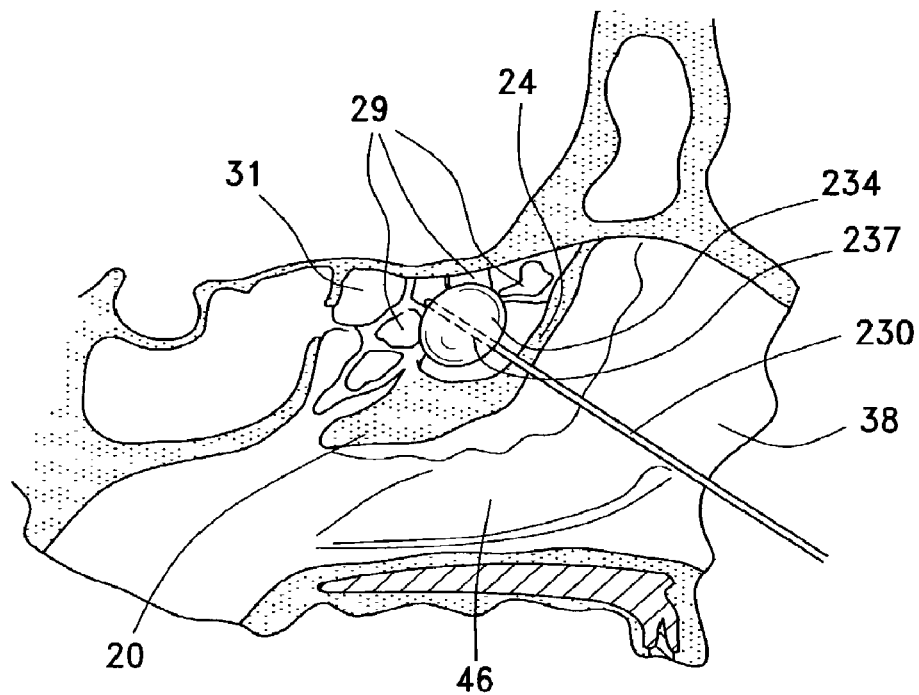
FIG. 12 is a schematic view of yet another step of the method of FIG. 10 showing the straight sinus balloon catheter dilating the ethmoid air cells and thus completing the anterior ethmoidectomy.

A balloon catheter ethmoidectomy of the anterior ethmoid sinus is shown in FIGS. 10-12. The middle turbinate 20 (FIG. 5) has been retracted medially to gain access to the middle meatus 22 (FIG. 5). In some cases, the middle turbinate may be partially or totally removed. The ethmoid infundibulum 24 is exposed by removing part of the uncinate process 26 (FIG. 4). A fine cutting forceps 66 is used to remove the anterior wall 30 of the ethmoid bulla 28 (FIG. 10). After anterior wall 30 of ethmoid bulla 28 is removed, the straight balloon catheter 230 is brought into nasal cavity 38, and distal segment 237 is pushed into bulla 28 (FIG. 11). Balloon 234 is inflated to 9 bars for 20 seconds then deflated. Balloon catheter 230 is then withdrawn from bulla 28. Distal segment 237 of balloon catheter 230 is then pushed into the anterior ethmoid air cells 29 which lie posterior to the previously removed ethmoid bulla 28 (FIG. 12). Balloon 234 is inflated to 9 bars for 20 seconds then deflated. Balloon catheter 230 is then slightly repositioned to insure thorough dilation and inflated again to 9 bars for 20 seconds, deflated, and removed from the area of anterior ethmoid cells 29.

Figure 13:
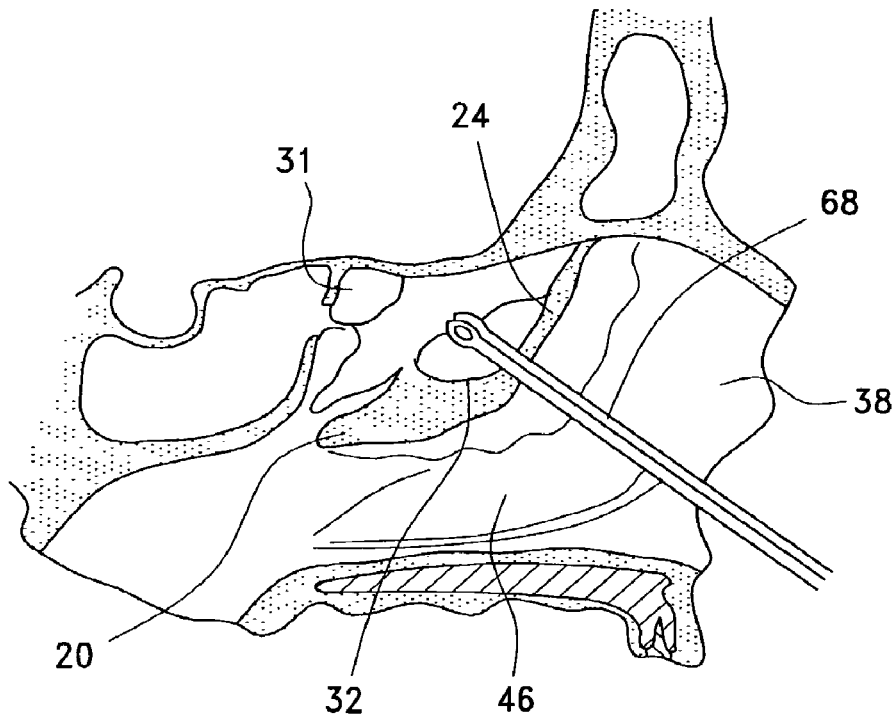
FIG. 13 is a schematic view of yet another step of the method of FIG. 10 showing a punch perforating the basal lamella of the middle turbinate.
Figure 14:
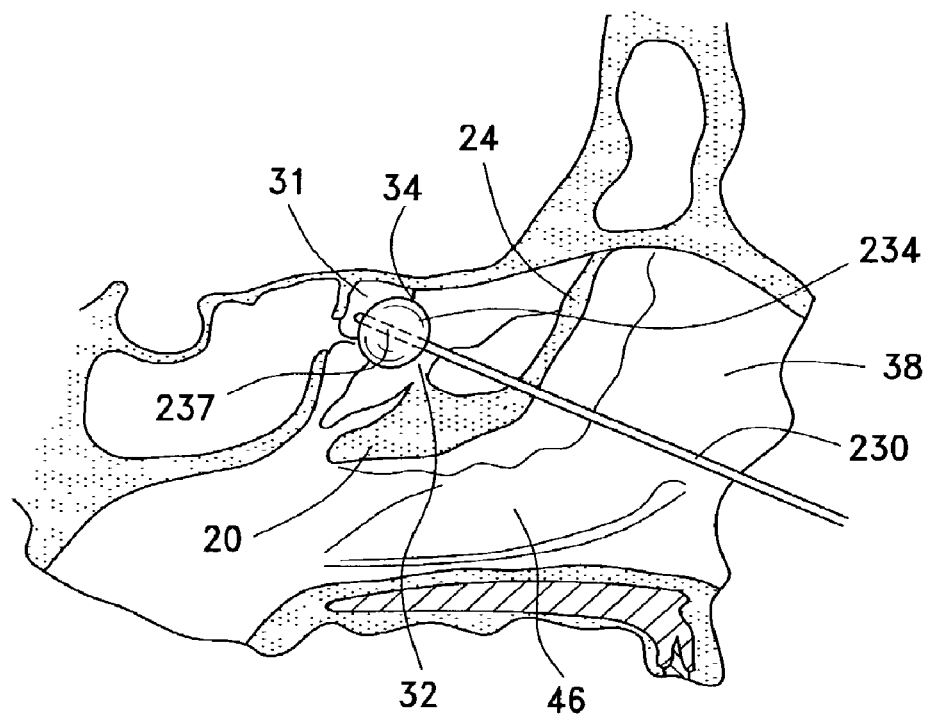
FIG. 14 is a schematic view of still another step of the method of FIG. 10 showing the straight sinus balloon catheter dilating the posterior ethmoid air cells and thus completing the posterior ethmoidectomy.

FIGS. 13 and 14 illustrate an ethmoidectomy of the posterior ethmoid sinus. When the posterior ethmoid sinus cells 31 must be removed, the basal lamella 32 of the middle turbinate 20 is perforated with a punch 68 (FIG. 13). Distal segment 237 of balloon catheter 230 is then pushed through the new opening 34 in the basal lamella 32 of the middle turbinate 20 into the posterior ethmoid air cells 31 and inflated 9 bars for 20 seconds (FIG. 14). Balloon catheter 230 is then deflated, slightly repositioned, and again inflated 9 bars for 20 seconds. Balloon catheter 230 is then deflated and withdrawn.

Figure 15:
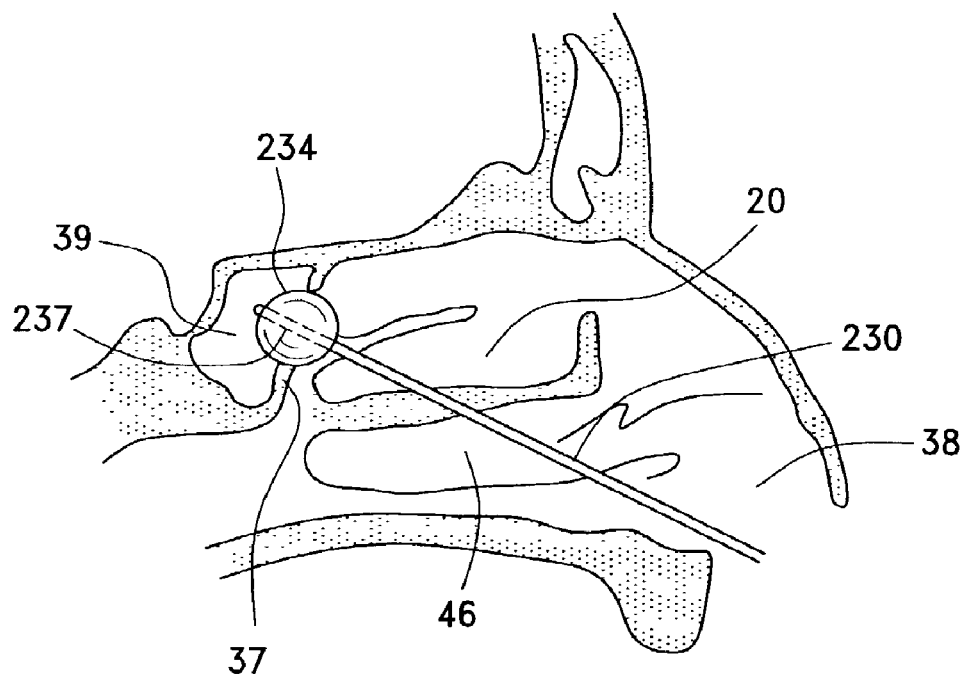
FIG. 15 is a schematic view of an additional step of the method of FIG. 10 showing the sinus balloon catheter dilating the anterior wall of the sphenoid sinus.

FIG. 15 shows sinusotomy of the sphenoid sinus. After anterior and posterior ethmoidectomy, distal segment 237 of balloon catheter 230 is inserted through the anterior wall 37 of sphenoid sinus 39 (FIG. 15). The balloon 234 is then inflated to 9 bars for 20 seconds then deflated. The balloon catheter 230 is slightly repositioned to insure thorough dilation and inflated again to 9 bars for 20 seconds, then deflated, and withdrawn.

Figure 16:
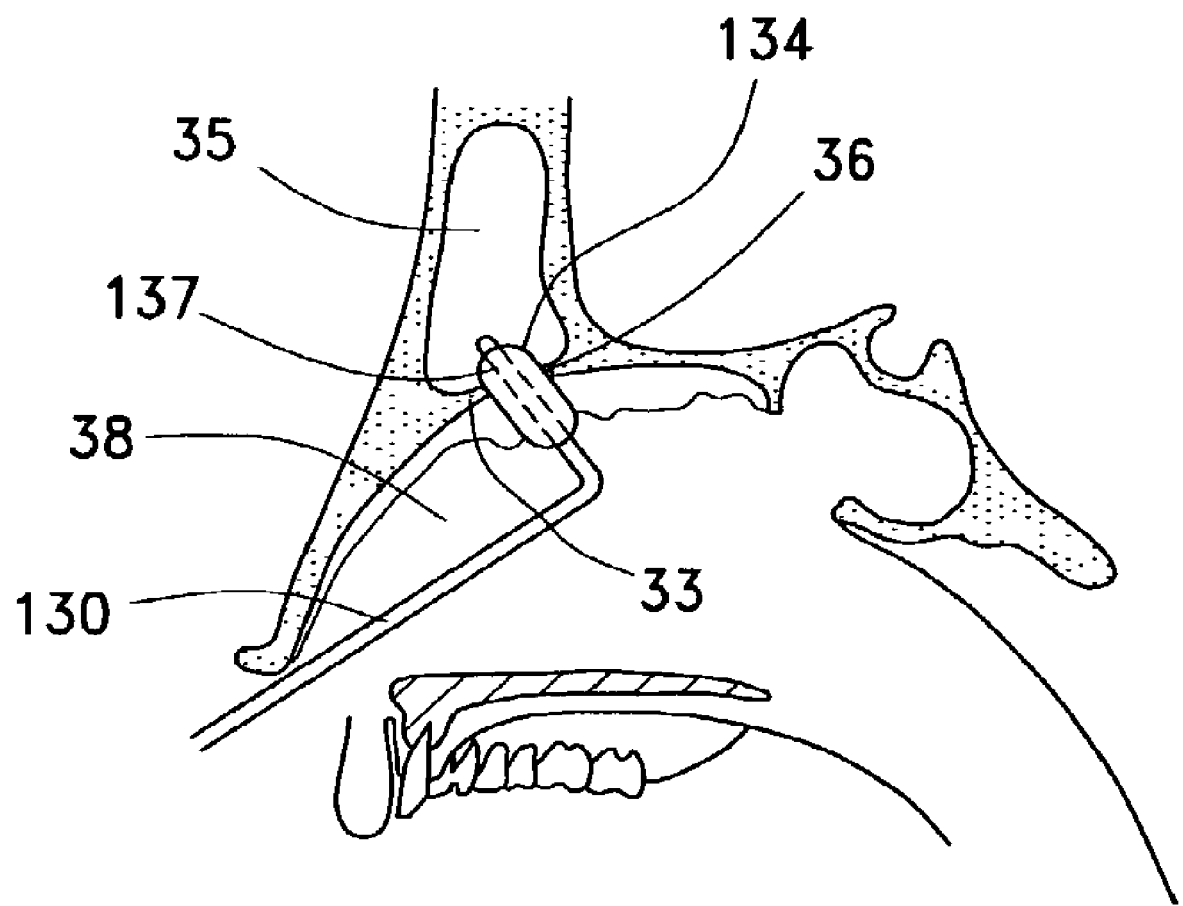
FIG. 16 if a schematic view of a further step of the method of FIG. 10 showing the angled sinus balloon catheter dilating the frontonasal duct.

FIG. 16 illustrates sinusotomy of the frontal sinus. After an anterior ethmoidectomy the nasofrontal duct 36 is exposed and in the surgeon's view. The distal segment 137 of an angled catheter 130 with a 5 mm inflated working diameter is brought into the frontnasal duct 36 and inflated to 9 bars, then deflated. The distal segment 137 of the balloon catheter 130 is slightly repositioned to insure complete dilation of the nasofrontal duct 36 and inflated to 9 bars for 20 seconds then deflated and withdrawn.

All of the above procedures may be performed in a similar fashion in patients who have had previous sinus surgery and the sinus openings have been obstructed by scar tissue or granulation tissue.

What is claimed is:

1. A method of treating a space in a patient's ethmoid sinus, comprising:
providing a catheter device comprising an expandable and contractible member which is expandable from a first smaller contracted profile to a second larger expanded profile;
creating an opening into the ethmoid sinus;
during the same medical procedure, pushing said member while in said contracted profile through the opening into the space associated with the ethmoid sinus of said patient;

expanding said member to said expanded profile to enlarge the space, the space being enlarged when the member is expanded; and removing the catheter from the now enlarged space, which remains enlarged for a period of time effective to treat the space associated with the ethmoid sinus after the balloon catheter is removed.

2. The method of claim 1, wherein said space is formed in the patient's ethmoid bulla.

3. The method of claim 2, which further comprises:
removing the anterior wall of the ethmoid bulla.

4. The method of claim 1, which further comprises:
medially retracting the patient's middle turbinate; and
removing a part of the patient's uncinate process.

5. The method of claim 2, which further comprises:
contracting said member after said expanding; and
completing removal of the ethmoid bulla.

6. The method of claim 1, which further comprises:
pushing said contracted member into the patient's anterior ethmoid air cells;
expanding said member to dilate said anterior ethmoid air cells; and
withdrawing said member from the space formerly occupied by said anterior ethmoid air cells.

7. The method of claim 1, which further comprises:
creating an opening in the patient's basal lamella of the patient's middle turbinate;
pushing said contracted member through said opening into said posterior ethmoid air cells;
expanding said member to dilate said posterior ethmoid cells; and
withdrawing said member from the space formerly occupied by said posterior ethmoid air cells.

8. The method of claim 1, which further comprises:
inserting said contracted member through an anterior wall of the patient's sphenoid sinus; and
expanding said member to dilate the anterior wall of the patient's sphenoid sinus.

9. The method of claim 1, which further comprises:
pushing said contracted member into a patient's nasofrontal duct; and
expanding said contracted member to dilate said nasofrontal duct.

10. The method of claim 1, wherein the catheter has sufficient stiffness and column strength that the contracted member can be pushed into the space.

11. The method of claim 1, wherein said member is located on a distal segment of the catheter, and wherein said distal segment is at an angle of between about one hundred thirty degrees and about one hundred eighty degrees to a proximal segment of the catheter.

12. The method of claim 11, wherein the angle is about one hundred eighty degrees.

13. The method of claim 1, further comprising:
inflating the member to about nine atmospheres.

14. The method of claim 1, further comprising:
contracting the member;
repositioning the member after the contracting; and
expanding the member after the repositioning.

15. The method of claim 1, which further comprises:
selecting the catheter device such that the member when in a contracted profile will fit snugly with the space.

16. The method of claim 1, which further comprises:
removing the patient's middle turbinate.

* * * * *